United States Patent
Melsky

(10) Patent No.: US 8,702,688 B2
(45) Date of Patent: Apr. 22, 2014

(54) CARDIAC ABLATION IMAGE ANALYSIS SYSTEM AND PROCESS

(75) Inventor: Gerald Melsky, Lexington, MA (US)

(73) Assignee: CardioFocus, Inc., Marlborough, MA (US)

( * ) Notice: Subject to any disclaimer, the term of this patent is extended or adjusted under 35 U.S.C. 154(b) by 235 days.

(21) Appl. No.: 12/899,218

(22) Filed: Oct. 6, 2010

(65) Prior Publication Data

US 2011/0082451 A1    Apr. 7, 2011

Related U.S. Application Data

(60) Provisional application No. 61/249,182, filed on Oct. 6, 2009.

(51) Int. Cl.
*A61B 18/18*    (2006.01)

(52) U.S. Cl.
USPC ............................... 606/14; 606/11

(58) Field of Classification Search
USPC ........................ 606/11–12, 14–15; 600/109
IPC ....................................................... A61B 18/18
See application file for complete search history.

(56) References Cited

U.S. PATENT DOCUMENTS

| | | | |
|---|---|---|---|
| 3,417,745 A | 12/1968 | Sheldon | |
| 3,821,510 A | 6/1974 | Muncheryan | |
| 4,224,929 A | 9/1980 | Furihata et al. | |
| 4,233,493 A | 11/1980 | Nath et al. | |
| 4,273,109 A | 6/1981 | Enderby | |
| 4,336,809 A | 6/1982 | Clark | |
| 4,445,892 A | 5/1984 | Hussein et al. | |
| 4,585,298 A | 4/1986 | Mori et al. | |
| 4,625,724 A | 12/1986 | Suzuki et al. | |
| 4,660,925 A | 4/1987 | McCaughan, Jr. | |
| 4,701,166 A | 10/1987 | Groshong et al. | |
| 4,718,417 A | 1/1988 | Kittrell et al. | |
| 4,770,653 A | 9/1988 | Shturman | |
| 4,781,681 A | 11/1988 | Sharrow et al. | |
| 4,819,632 A | 4/1989 | Davies et al. | |
| 4,842,390 A | 6/1989 | Sottini et al. | |

(Continued)

FOREIGN PATENT DOCUMENTS

| | | |
|---|---|---|
| DE | 94117543 | 11/1994 |
| EP | 0214712 | 3/1987 |

(Continued)

OTHER PUBLICATIONS

Reddy et al., View-Synchronized Robotic Image-Guided Therapy for Atrial Fibrillation Ablation Experimental Validation and Clinical Feasibility, Circulation. 2007;115:2705-2714.*

(Continued)

*Primary Examiner* — Bill Thomson
*Assistant Examiner* — Manolis Pahakis
(74) *Attorney, Agent, or Firm* — Leason Ellis LLP

(57) ABSTRACT

A system is provided for identifying the sufficiency of lesions formed during a tissue ablation procedure. The system captures live and still images from the surgical site and provides composite imaging to the operator. Through the use of the system, the aiming light used to direct ablative energy is captured on the still images and used to indicate locations in a surgical site where energy has been directed. Through the use of processing modules, the system can analyze the lesions and determine the sufficiency thereof.

11 Claims, 8 Drawing Sheets

(56) References Cited

U.S. PATENT DOCUMENTS

| | | | |
|---|---|---|---|
| 4,852,567 A | 8/1989 | Sinofsky | |
| 4,860,743 A | 8/1989 | Abela | |
| 4,862,886 A | 9/1989 | Clarke et al. | |
| 4,878,492 A | 11/1989 | Sinofsky et al. | |
| 4,878,725 A | 11/1989 | Hessel et al. | |
| 4,913,142 A * | 4/1990 | Kittrell et al. | 606/7 |
| 4,961,738 A | 10/1990 | Mackin | |
| 5,026,367 A | 6/1991 | Leckrone et al. | |
| 5,030,201 A | 7/1991 | Palestrant | |
| 5,053,033 A | 10/1991 | Clarke | |
| 5,071,417 A | 12/1991 | Sinofsky | |
| 5,078,681 A | 1/1992 | Kawashima et al. | |
| 5,090,959 A | 2/1992 | Samson et al. | |
| 5,098,426 A * | 3/1992 | Sklar et al. | 606/5 |
| 5,109,859 A | 5/1992 | Jenkins | |
| 5,125,925 A | 6/1992 | Lundahl | |
| 5,133,709 A | 7/1992 | Prince | |
| 5,140,987 A | 8/1992 | Schuger et al. | |
| 5,151,096 A | 9/1992 | Khoury | |
| 5,151,097 A | 9/1992 | Daikuzono et al. | |
| 5,163,935 A | 11/1992 | Black et al. | |
| 5,169,395 A | 12/1992 | Narciso, Jr. | |
| 5,188,632 A | 2/1993 | Goldenberg | |
| 5,188,634 A | 2/1993 | Hussein et al. | |
| 5,190,538 A | 3/1993 | Hussein et al. | |
| 5,196,005 A | 3/1993 | Doiron et al. | |
| 5,207,699 A | 5/1993 | Coe | |
| 5,209,748 A | 5/1993 | Daikuzono | |
| 5,219,346 A | 6/1993 | Wagnieres et al. | |
| 5,242,438 A | 9/1993 | Saadatmanesh et al. | |
| 5,261,904 A | 11/1993 | Baker et al. | |
| 5,269,777 A | 12/1993 | Doiron et al. | |
| RE34,544 E | 2/1994 | Spears | |
| 5,318,024 A | 6/1994 | Kittrell et al. | |
| 5,330,465 A | 7/1994 | Doiron et al. | |
| 5,337,381 A | 8/1994 | Biswas et al. | |
| 5,350,375 A | 9/1994 | Deckelbaum et al. | |
| 5,363,458 A | 11/1994 | Pan et al. | |
| 5,368,564 A | 11/1994 | Savage | |
| 5,374,953 A * | 12/1994 | Sasaki et al. | 348/65 |
| 5,380,316 A | 1/1995 | Aita et al. | |
| 5,380,317 A | 1/1995 | Everett et al. | |
| 5,395,362 A | 3/1995 | Sacharoff et al. | |
| 5,401,270 A | 3/1995 | Muller et al. | |
| 5,409,483 A | 4/1995 | Campbell et al. | |
| 5,417,653 A | 5/1995 | Sahota et al. | |
| 5,418,649 A | 5/1995 | Igarashi | |
| 5,423,805 A | 6/1995 | Brucker et al. | |
| 5,427,119 A | 6/1995 | Swartz et al. | |
| 5,431,647 A | 7/1995 | Purcell, Jr. et al. | |
| 5,437,660 A | 8/1995 | Johnson et al. | |
| 5,441,497 A | 8/1995 | Narciso, Jr. | |
| 5,445,608 A | 8/1995 | Chen et al. | |
| 5,464,404 A | 11/1995 | Abela et al. | |
| 5,482,037 A | 1/1996 | Borghi et al. | |
| 5,496,305 A | 3/1996 | Kittrell et al. | |
| 5,497,774 A | 3/1996 | Swartz et al. | |
| 5,507,725 A | 4/1996 | Savage et al. | |
| 5,531,664 A * | 7/1996 | Adachi et al. | 600/149 |
| 5,536,265 A | 7/1996 | van den Bergh et al. | |
| 5,575,766 A | 11/1996 | Swartz et al. | |
| 5,605,162 A | 2/1997 | Mirzaee et al. | |
| 5,613,965 A | 3/1997 | Muller | |
| 5,643,253 A | 7/1997 | Baxter et al. | |
| 5,649,923 A | 7/1997 | Gregory et al. | |
| 5,653,706 A * | 8/1997 | Zavislan et al. | 606/9 |
| 5,662,712 A | 9/1997 | Pathak et al. | |
| 5,680,860 A | 10/1997 | Imran | |
| 5,690,611 A | 11/1997 | Swartz et al. | |
| 5,693,043 A | 12/1997 | Kittrell et al. | |
| 5,700,243 A | 12/1997 | Narciso, Jr. | |
| 5,702,438 A | 12/1997 | Avitall | |
| 5,722,401 A | 3/1998 | Pietroski et al. | |
| 5,725,522 A | 3/1998 | Sinofsky | |
| 5,759,619 A | 6/1998 | Jin | |
| 5,769,843 A | 6/1998 | Abela et al. | |
| 5,772,590 A | 6/1998 | Webster, Jr. | |
| 5,773,835 A | 6/1998 | Sinofsky | |
| 5,779,646 A | 7/1998 | Koblish et al. | |
| 5,782,239 A | 7/1998 | Webster, Jr. | |
| 5,782,899 A | 7/1998 | Imran | |
| 5,800,482 A | 9/1998 | Pomeranz et al. | |
| 5,807,395 A | 9/1998 | Mulier et al. | |
| 5,823,955 A | 10/1998 | Kuck et al. | |
| 5,824,005 A | 10/1998 | Motamedi et al. | |
| 5,827,190 A * | 10/1998 | Palcic et al. | 600/476 |
| 5,830,209 A | 11/1998 | Savage et al. | |
| 5,833,682 A | 11/1998 | Amplatz et al. | |
| 5,843,073 A | 12/1998 | Sinofsky | |
| 5,845,646 A * | 12/1998 | Lemelson | 128/899 |
| 5,860,974 A | 1/1999 | Abele | |
| 5,885,278 A | 3/1999 | Fleischman | |
| 5,891,133 A | 4/1999 | Murphy-Chutorian | |
| 5,891,134 A | 4/1999 | Goble et al. | |
| 5,904,651 A * | 5/1999 | Swanson et al. | 600/407 |
| 5,908,415 A | 6/1999 | Sinofsky | |
| 5,931,834 A | 8/1999 | Murphy-Chutorian et al. | |
| 5,938,660 A | 8/1999 | Swartz et al. | |
| 5,947,959 A | 9/1999 | Sinofsky | |
| 5,967,984 A | 10/1999 | Chu et al. | |
| 5,971,983 A | 10/1999 | Lesh | |
| 5,995,875 A | 11/1999 | Blewett et al. | |
| 6,004,269 A | 12/1999 | Crowley et al. | |
| 6,012,457 A | 1/2000 | Lesh | |
| 6,024,740 A | 2/2000 | Lesh et al. | |
| 6,056,744 A | 5/2000 | Edwards | |
| 6,064,902 A | 5/2000 | Haissaguerre et al. | |
| 6,071,279 A | 6/2000 | Whayne et al. | |
| 6,071,281 A | 6/2000 | Burnside et al. | |
| 6,071,282 A | 6/2000 | Fleischman | |
| 6,071,302 A | 6/2000 | Sinofsky et al. | |
| 6,086,581 A | 7/2000 | Reynolds et al. | |
| 6,090,084 A | 7/2000 | Hassett et al. | |
| 6,099,514 A | 8/2000 | Sharkey et al. | |
| 6,102,905 A | 8/2000 | Baxter et al. | |
| 6,117,071 A | 9/2000 | Ito et al. | |
| 6,117,101 A | 9/2000 | Diederich et al. | |
| 6,120,496 A | 9/2000 | Whayne et al. | |
| 6,129,667 A * | 10/2000 | Dumoulin et al. | 600/424 |
| 6,146,379 A | 11/2000 | Fleischman et al. | |
| 6,159,203 A | 12/2000 | Sinofsky | |
| 6,161,543 A | 12/2000 | Cox et al. | |
| 6,164,283 A | 12/2000 | Lesh | |
| 6,179,835 B1 | 1/2001 | Panescu et al. | |
| 6,214,002 B1 | 4/2001 | Fleischman et al. | |
| 6,217,510 B1 | 4/2001 | Ozawa et al. | |
| 6,235,025 B1 | 5/2001 | Swartz et al. | |
| 6,237,605 B1 | 5/2001 | Vaska et al. | |
| 6,240,231 B1 | 5/2001 | Ferrera et al. | |
| 6,245,064 B1 | 6/2001 | Lesh et al. | |
| 6,251,092 B1 | 6/2001 | Qin et al. | |
| 6,251,109 B1 | 6/2001 | Hassett et al. | |
| 6,254,599 B1 | 7/2001 | Lesh et al. | |
| 6,270,492 B1 | 8/2001 | Sinofsky | |
| 6,305,378 B1 | 10/2001 | Lesh | |
| 6,312,427 B1 | 11/2001 | Berube et al. | |
| 6,314,962 B1 | 11/2001 | Vaska et al. | |
| 6,325,797 B1 | 12/2001 | Stewart et al. | |
| 6,352,531 B1 | 3/2002 | O'Connor et al. | |
| 6,383,151 B1 | 5/2002 | Diederich et al. | |
| 6,394,949 B1 | 5/2002 | Crowley et al. | |
| 6,416,511 B1 | 7/2002 | Lesh et al. | |
| 6,423,055 B1 | 7/2002 | Farr et al. | |
| 6,423,058 B1 | 7/2002 | Edwards et al. | |
| 6,436,127 B1* | 8/2002 | Anderson et al. | 607/89 |
| 6,471,697 B1 | 10/2002 | Lesh | |
| 6,485,485 B1 | 11/2002 | Winston et al. | |
| 6,500,174 B1 | 12/2002 | Maguire et al. | |
| 6,502,576 B1 | 1/2003 | Lesh | |
| 6,503,247 B2 | 1/2003 | Swartz et al. | |
| 6,514,249 B1 | 2/2003 | Maguire et al. | |
| 6,522,933 B2 | 2/2003 | Nguyen | |
| 6,544,262 B2 | 4/2003 | Fleischman | |
| 6,547,780 B1 | 4/2003 | Sinofsky | |

(56) References Cited

U.S. PATENT DOCUMENTS

| | | | |
|---|---|---|---|
| 6,554,794 B1 | 4/2003 | Mueller et al. | |
| 6,558,375 B1 | 5/2003 | Sinofsky et al. | |
| 6,562,020 B1 | 5/2003 | Constantz et al. | |
| 6,572,609 B1 | 6/2003 | Farr et al. | |
| 6,579,278 B1 | 6/2003 | Bencini | |
| 6,579,285 B2 | 6/2003 | Sinofsky | |
| 6,582,536 B2 | 6/2003 | Shimada | |
| 6,605,055 B1 | 8/2003 | Sinofsky et al. | |
| 6,605,084 B2 | 8/2003 | Acker et al. | |
| 6,626,900 B1 | 9/2003 | Sinofsky et al. | |
| 6,633,773 B1* | 10/2003 | Reisfeld | 600/407 |
| 6,635,054 B2 | 10/2003 | Fjield et al. | |
| 6,648,875 B2 | 11/2003 | Simpson et al. | |
| 6,650,927 B1* | 11/2003 | Keidar | 600/424 |
| 6,669,655 B1 | 12/2003 | Acker et al. | |
| 6,676,654 B1* | 1/2004 | Balle-Petersen et al. | 606/9 |
| 6,676,656 B2 | 1/2004 | Sinofsky | |
| 6,679,873 B2 | 1/2004 | Rabiner et al. | |
| 6,702,780 B1 | 3/2004 | Gilboa et al. | |
| 6,771,996 B2 | 8/2004 | Bowe et al. | |
| 6,896,673 B2 | 5/2005 | Hooven | |
| 6,907,298 B2 | 6/2005 | Smits et al. | |
| 6,916,306 B1 | 7/2005 | Jenkins et al. | |
| 6,932,809 B2 | 8/2005 | Sinofsky | |
| 6,942,657 B2 | 9/2005 | Sinofsky et al. | |
| 6,953,457 B2 | 10/2005 | Farr et al. | |
| 6,997,924 B2 | 2/2006 | Schwartz et al. | |
| 7,001,383 B2* | 2/2006 | Keidar | 606/41 |
| 7,113,831 B2* | 9/2006 | Hooven | 607/101 |
| 7,207,984 B2 | 4/2007 | Farr et al. | |
| 7,217,266 B2* | 5/2007 | Anderson et al. | 606/12 |
| 7,250,048 B2* | 7/2007 | Francischelli et al. | 606/32 |
| 7,252,664 B2* | 8/2007 | Nasab et al. | 606/34 |
| 7,338,485 B2* | 3/2008 | Brucker et al. | 606/12 |
| 7,357,796 B2 | 4/2008 | Farr et al. | |
| 7,367,972 B2* | 5/2008 | Francischelli et al. | 606/34 |
| 7,594,925 B2* | 9/2009 | Danek et al. | 607/96 |
| 7,662,152 B2* | 2/2010 | Sharareh et al. | 606/41 |
| 7,706,860 B2* | 4/2010 | McGee | 600/424 |
| 7,715,604 B2* | 5/2010 | Sun et al. | 382/128 |
| 7,935,108 B2 | 5/2011 | Baxter et al. | |
| 8,025,661 B2 | 9/2011 | Arnold et al. | |
| 2001/0025174 A1* | 9/2001 | Daniel et al. | 606/15 |
| 2001/0030107 A1 | 10/2001 | Simpson | |
| 2002/0019627 A1 | 2/2002 | Maguire et al. | |
| 2002/0029062 A1 | 3/2002 | Satake | |
| 2002/0065512 A1 | 5/2002 | Fjield et al. | |
| 2002/0091383 A1 | 7/2002 | Hooven | |
| 2002/0107511 A1 | 8/2002 | Collins et al. | |
| 2002/0115995 A1 | 8/2002 | Lesh et al. | |
| 2002/0120264 A1 | 8/2002 | Crowley et al. | |
| 2002/0183729 A1 | 12/2002 | Farr et al. | |
| 2002/0183739 A1 | 12/2002 | Long | |
| 2003/0050632 A1 | 3/2003 | Fjield et al. | |
| 2003/0065307 A1 | 4/2003 | Lesh | |
| 2003/0069620 A1 | 4/2003 | Li | |
| 2003/0111085 A1 | 6/2003 | Lesh | |
| 2003/0120270 A1 | 6/2003 | Acker | |
| 2003/0144657 A1 | 7/2003 | Bowe et al. | |
| 2003/0158550 A1 | 8/2003 | Ganz et al. | |
| 2003/0171746 A1 | 9/2003 | Fleischman | |
| 2004/0006333 A1 | 1/2004 | Arnold et al. | |
| 2004/0054360 A1 | 3/2004 | Schwartz et al. | |
| 2004/0059397 A1 | 3/2004 | Sinofsky et al. | |
| 2004/0122290 A1 | 6/2004 | Irion et al. | |
| 2005/0038419 A9 | 2/2005 | Arnold et al. | |
| 2005/0065471 A1* | 3/2005 | Kuntz | 604/133 |
| 2005/0065504 A1 | 3/2005 | Melsky et al. | |
| 2005/0075629 A1* | 4/2005 | Chapelon et al. | 606/41 |
| 2005/0143793 A1* | 6/2005 | Korman et al. | 607/94 |
| 2005/0234436 A1* | 10/2005 | Baxter et al. | 606/14 |
| 2005/0234437 A1* | 10/2005 | Baxter et al. | 606/15 |
| 2005/0288654 A1 | 12/2005 | Nieman et al. | |
| 2006/0122587 A1* | 6/2006 | Sharareh | 606/11 |
| 2006/0247683 A1* | 11/2006 | Danek et al. | 607/2 |
| 2006/0253113 A1 | 11/2006 | Arnold et al. | |
| 2007/0073278 A1* | 3/2007 | Johnson et al. | 606/11 |
| 2007/0078451 A1 | 4/2007 | Arnold et al. | |
| 2008/0015562 A1* | 1/2008 | Hong et al. | 606/34 |
| 2008/0015569 A1* | 1/2008 | Saadat et al. | 606/41 |
| 2008/0033410 A1* | 2/2008 | Rastegar et al. | 606/9 |
| 2008/0039746 A1 | 2/2008 | Hissong et al. | |
| 2008/0108870 A1* | 5/2008 | Wiita et al. | 600/112 |
| 2008/0195088 A1 | 8/2008 | Farr et al. | |
| 2009/0005768 A1* | 1/2009 | Sharareh et al. | 606/17 |
| 2009/0221996 A1 | 9/2009 | Lesh | |
| 2009/0221997 A1 | 9/2009 | Arnold et al. | |
| 2009/0275934 A1 | 11/2009 | Baxter et al. | |
| 2009/0299354 A1 | 12/2009 | Melsky et al. | |
| 2009/0326320 A1* | 12/2009 | Sinofsky et al. | 600/109 |
| 2010/0168738 A1* | 7/2010 | Schneider et al. | 606/41 |
| 2011/0082449 A1 | 4/2011 | Melsky et al. | |
| 2011/0082450 A1 | 4/2011 | Melsky et al. | |
| 2011/0082451 A1 | 4/2011 | Melsky | |
| 2011/0082452 A1 | 4/2011 | Melsky et al. | |
| 2011/0118714 A1* | 5/2011 | Deladi et al. | 606/10 |
| 2011/0245822 A1 | 10/2011 | Baxter et al. | |
| 2011/0245828 A1 | 10/2011 | Baxter et al. | |

FOREIGN PATENT DOCUMENTS

| | | |
|---|---|---|
| EP | 0292621 | 11/1988 |
| EP | 0292695 | 11/1988 |
| EP | 0299448 | 1/1989 |
| EP | 0311458 | 4/1989 |
| EP | 0437181 | 7/1991 |
| EP | 0437183 | 7/1991 |
| EP | 0439629 | 8/1991 |
| EP | 0598984 | 6/1994 |
| EP | 0792664 | 9/1997 |
| EP | 1072231 | 1/2001 |
| EP | 1331893 | 12/2004 |
| FR | 2798371 A | 3/2001 |
| JP | 2003-210028 A | 7/2003 |
| JP | 2004-065076 A | 3/2004 |
| WO | WO 9217243 | 10/1992 |
| WO | WO 9306888 | 4/1993 |
| WO | WO 9319680 | 10/1993 |
| WO | WO 9325155 | 12/1993 |
| WO | WO 9417434 | 8/1994 |
| WO | WO 9426184 | 11/1994 |
| WO | WO 9607451 | 3/1996 |
| WO | WO 9634646 | 11/1996 |
| WO | WO 9640342 | 12/1996 |
| WO | WO 9737714 | 10/1997 |
| WO | WO 00/67656 | 11/2000 |
| WO | WO 00/67832 | 11/2000 |
| WO | WO 01/03599 A2 | 1/2001 |
| WO | WO 0113812 | 3/2001 |
| WO | WO 0103599 A3 * | 5/2001 |
| WO | WO 01/64123 | 9/2001 |
| WO | WO 02/096479 | 12/2002 |
| WO | WO 03090835 | 11/2003 |
| WO | WO 2004-110258 | 12/2004 |

OTHER PUBLICATIONS

Eddins S, Steve on Image Processing, Mathworks Inc. Website, Aug. 20, 2008 http://blogs.mathworks.com/steve/2008/08/20/image-visualization-using-transparency/.*

Bredikis, J. et al. "Laser Destruction of the Atrioventricular Bundle Using the Cardiac Endoscope" Kardiologiia, 1988, 28(8): 94-96.

Chevalier, P. et al. "Thoracoscopic Epicardial Radiofrequency Ablation for Vagal Atrial Fibrillation in Dogs" PACE, 1999, 22: 880-886.

Froelich, J. et al. "Evaluation of a Prototype Steerable Angioscopic Laser Catheter in a Canine Model: A Feasibility Study" Cardiovasc Intervent Radiol, 1993 16: 235-238.

Fujimura, O. et al. "Direct in Vivo Visualization of Right Cardiac Anatomy by Fiberoptic Endoscopy" Angiology; 1995, 46 (3): 201-208.

Fujimura, O. et al. "Direct In Vivo Visualization of Right Cardiac Anatomy by Fiberoptic Endoscopy: Observation of Radiofrequency-

(56) References Cited

OTHER PUBLICATIONS

Induced Acute Lesions Around the Ostium of the Coronary Sinus" European Heart J., 1994, 15: 534-540.

Gamble, W. and Innis, R. "Experimental Intracardiac Visualization" NEJM, 1967, 276(25): 1397-1403.

Hirao, K. et al. "Transcatheter Neodymium—Yttrium—Aluminum—Garnet Laser Coagulation of Canine Ventricle Using a Balloon-Tipped Cardioscope" Jpn Circ J., 1997, 61: 695-703.

Keane, D. et al. "Pulmonary Vein Isolation for Atrial Fibrillation" Rev Cardiovasc Med., 2002, 3(4): 167-175.

Kuo, C. et al. "In Vivo Angioscopic Visualization of Right Heart Structure in Dogs by Means of a Balloon-Tipped Fiberoptic Endoscope: Potential Role in Percutaneous Ablative Procedures." American Heart J., 1994, 127: 187-197.

Nakagawa, H. et al. "Cardioscopic Catheter Ablation with Noncontact, Pulsed Nd:YAG Laser Using Saline Inflated Balloon Catheter," Presentation JACC 1998; 31: 118A-119A.

Obelienius, V. et al. "Transvenous Ablation of the Atrioventricular Conduction System by Laser Irradiation Under Endoscopic Control" Lasers in Surgery Medicine, 1985, 5: 469-474.

Roggan, A., et al. "Optical Properties of Circulating Human Blood in the Wavelength Range 400-2400 nm" J Biomedical Optics, 1999, 4(1): 36-46.

Saliba, W. et al. "Circumferential Ultrasound Ablation for Pulmonary Vein Isolation: Analysis of Acute and Chronic Failures" J Cardiovascular Electrophysiology, 2002, 13(10): 957-961.

Shure, D. et al. "Identification of Pulmonary Emboli in the Dog: Comparison of Angioscopy and Perfusion Scanning" Circulation, 1981, 64(3): 618-621.

Shure, D., et al. "Fiberoptic Angioscopy: Role in the Diagnosis of Chronic Pulmonary Arterial Obstruction" Ann Int Med., 1985, 103: 844-850.

Tanabe, T. et al. "Cardiovascular Fiberoptic Endoscopy: Development and Clinical Application" Surgery, 1980, 87(4): 375-379.

Tanaka, K. et al., "Endoscopy-Assisted Radiofrequency Ablation Around the Coronary Sinus Ostium in Dogs: Its Effects on Atrioventricular Nodal Properties and Ventricular Response During Atrial Fibrillation," Journal of Cardiovascular Electrophysiology, vol. 7, No. 11, Nov. 1996, pp. 1063-1073.

Uchida, Y. et al. "Fiberoptic Angioscopy of Cardiac Chambers, Valves, and Great Vessels Using a Guiding Balloon Catheter in Dogs." American Heart J., 1998, 115(6): 1297-1302.

Uchida, Y. et al. "Percutaneous Pulmonary Angioscopy Using a Guiding Balloon Catheter" Clin. Cardiol., 1988, 11: 143-148.

Vanermen, H. et al. "Minimally Invasive Video-Assisted Mitral Valve Surgery: From Port-Access Towards a Totally Endoscopic Procedure" J Card Surg., 2000, 15: 51-60.

Yamamoto, N. et al. "Nonfluoroscopic Guidance for Catheter Placement into the Coronary Sinus under Direct Vision Using a Balloon-Tipped Cardioscope" PACE, 1998; 21: 1724-1729.

\* cited by examiner

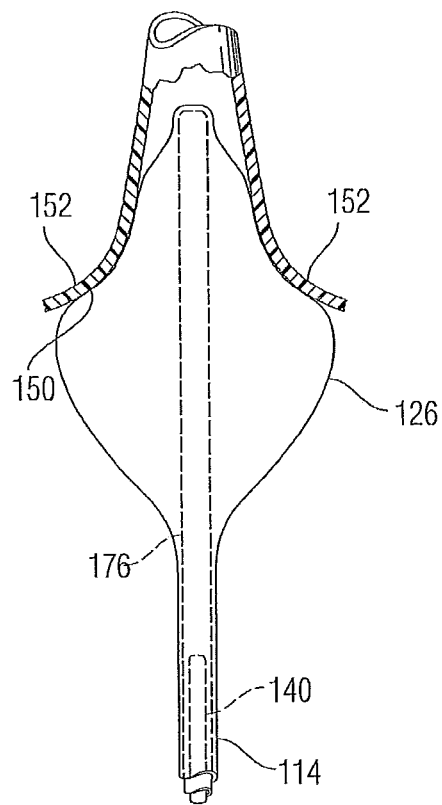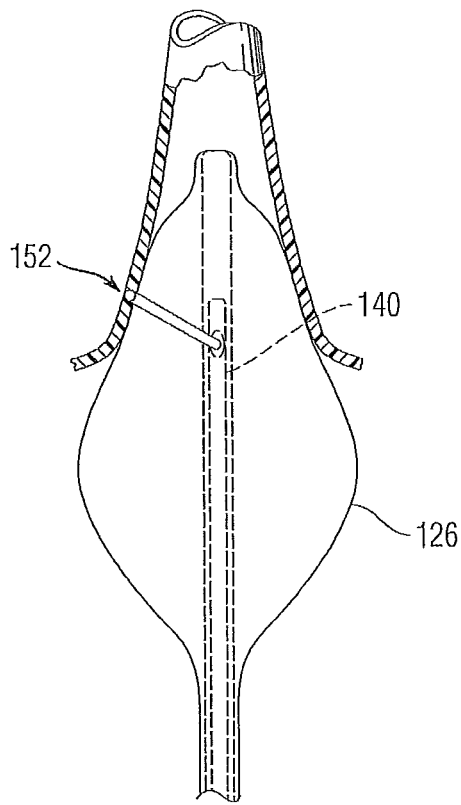
Fig. 5
Fig. 6

CARDIAC ABLATION IMAGE ANALYSIS SYSTEM AND PROCESS

RELATED APPLICATION

The present application claims the benefit of U.S. patent application Ser. No. 61/249,182, filed Oct. 6, 2009, which is hereby incorporated by reference in its entirety.

TECHNICAL FIELD

The present disclosure relates to cardiac ablation systems, and more particularly to a cardiac ablation system and process providing image analysis for determining the quality of lesions formed during a surgical ablation procedure.

BACKGROUND

Cardiac arrhythmias (e.g., fibrillation) are irregularities in the normal beating pattern of the heart and can manifest themselves in either the atria or the ventricles of the heart. For example, atrial fibrillation is a form of arrhythmia characterized by rapid randomized contractions of atrial myocardium, causing an irregular, often rapid ventricular rate. The regular pumping function of the atria is replaced by a disorganized, ineffective quivering as a result of chaotic conduction of electrical signals through the upper chambers of the heart. Atrial fibrillation is often associated with other forms of cardiovascular disease, including congestive heart failure, rheumatic heart disease, coronary artery disease, left ventricular hypertrophy, cardiomyopathy, or hypertension.

It is now understood that recurrent atrial fibrillation (paroxysmal and persistent) is triggered by rapidly firing tissue, (called "ectopic foci"), that are located in one or more of the four pulmonary veins, which attach to the rear of the left atrium. It has been found that atrial fibrillation may be cured by electrically isolating the pulmonary veins from the rest of the atrium.

Various techniques have been employed for pulmonary vein isolation. A common purpose of each of these techniques is to replace cardiac muscle cells with scar tissue, which scar tissue cannot conduct normal electrical activity within the heart.

In one known approach, circumferential ablation of tissue within the pulmonary veins has been practiced to treat atrial fibrillation. By ablating the heart tissue at selected locations, electrical conductivity from one segment to another can be blocked and the resulting segments become too small to sustain the fibrillatory process on their own.

Several types of ablation devices have recently been proposed for creating lesions to treat cardiac arrhythmias. Many of the recently proposed ablation instruments are percutaneous devices that are designed to create such lesions from within the heart. Such devices are positioned in the heart by catheterization of the patient, e.g., by passing the ablation instrument into the heart via a blood vessel, such as the femoral vein.

Typically, percutaneous devices are positioned with the assistance of a guide wire, which is first advanced into heart. In one common approach, a guide wire or similar guide device is advanced through the left atrium of the heart and into a pulmonary vein. A catheter instrument with an expandable element is then advanced over the guide wire and into the pulmonary vein where the expandable element (e.g., a balloon) is inflated. The balloon includes a circumferential ablation element, e.g., an energy emitting device, such as a laser, disposed in the inner surface of the balloon, which performs the ablation procedure.

It is noted that ablation within the pulmonary vein can result in complications. Overtreatment deep within a vein can result in stenosis (closure of the vein itself), necrosis or other structural damage, any of which can necessitate immediate open chest surgery. Conversely, undertreatment in which scar tissue formed is not continuous and/or insufficient to replace the cardiac muscles sought to be electrically isolated from the atrium will cause the surgical ablation procedure to be unsuccessful. Thus, repeating of the surgical ablation procedure is then required which is almost always undesirable. The term "continuous" in the context of a lesion is intended to mean a lesion that substantially blocks electrical conduction between tissue segments on opposite sides of the lesion.

SUMMARY

In accordance with a broad aspect of the invention, the present invention provides for a cardiac ablation system that allows for a user or operator to generate a record of the locations within a surgical site, wherein sufficient ablative energy has been directed. The tissue ablation system is electronically coupled to a tissue ablation instrument which forms lesions on tissue. The tissue ablation system includes a processing system for determining the sufficiency of lesions formed on tissue at a surgical site by evaluating operating data received from the tissue ablation instrument.

In more particular aspects, the present invention provides a system that records still and continuous video images from a surgical site with an image recording device. A colored aiming light, in conjunction with a white illuminating light, is used to direct ablative energy to tissue in need of treatment. The image recording device is used to transmit the image of the surgical site to an operator in real-time. Upon activation of the ablation laser, ablative energy is delivered to tissue. Immediately prior to delivery of the ablative energy, the image recording device records a still image from the live video feed. The still image is then depicted on a display next to the continuing live video feed of the surgical site. Due to the reflection of the aiming light, it is possible to identify where the energy was delivered (and where ablation has occurred). Therefore, the system allows a user to aim the ablative energy emission at another area of the surgical site that needs treatment (e.g., a gap in lesion), without the danger of overtreating an area of the surgical site. Furthermore, each time ablative energy is delivered, another still image is taken during the activation and that image is overlaid on the previous still image. The transparency of each image can be modified so that the aiming marker native to each image will be visible through the image layers. In this way, a user can construct a time or emission based map of the treated areas in a surgical site.

The advantages of this system are apparent. The cardiac ablation system envisioned uses live and still imagery to view a surgical site. By providing an aiming light, the user is able to determine where the ablative energy will be deposited. Furthermore, by recording an image of the surgical site at the time of depositing, the user has a record of which areas have been treated. Additionally, by overlaying a series of images taken during discrete ablative treatments, a user can construct a track or trace of the path of the energy at the surgical site. This allows the user to view the surgical site without obstruction, with the confidence that no excessive or damaging energy will be deposited to locations where it is not needed or already treated. The system further enables a user to create a time-lapse map of the path taken or the order of lesions treated.

These and other aspects, features and benefits of the invention can be further appreciated from the accompanying drawings, which illustrate certain embodiments of the invention together with the detailed description thereof.

BRIEF DESCRIPTION OF THE DRAWINGS

The objects and features of the invention may be understood with reference to the following detailed description of an illustrative embodiment of the present invention taken together in conjunction with the accompanying drawings in which:

FIG. 5 is a schematic view of the cardiac ablation instrument of FIG. 2 shown in a treatment position at a surgical site in the pulmonary vein;

FIG. 6 is a schematic view of the cardiac ablation instrument of FIG. 2 with its compliant balloon inflated and its ablation element deployed at one of a plurality of locations;

DETAILED DESCRIPTION OF CERTAIN EMBODIMENTS OF THE INVENTION

The present invention will now be described more fully with reference to the accompanying drawings, in which illustrated embodiments of the present invention are shown. The present invention is not limited in any way to any of the illustrated embodiments.

Figure 1:
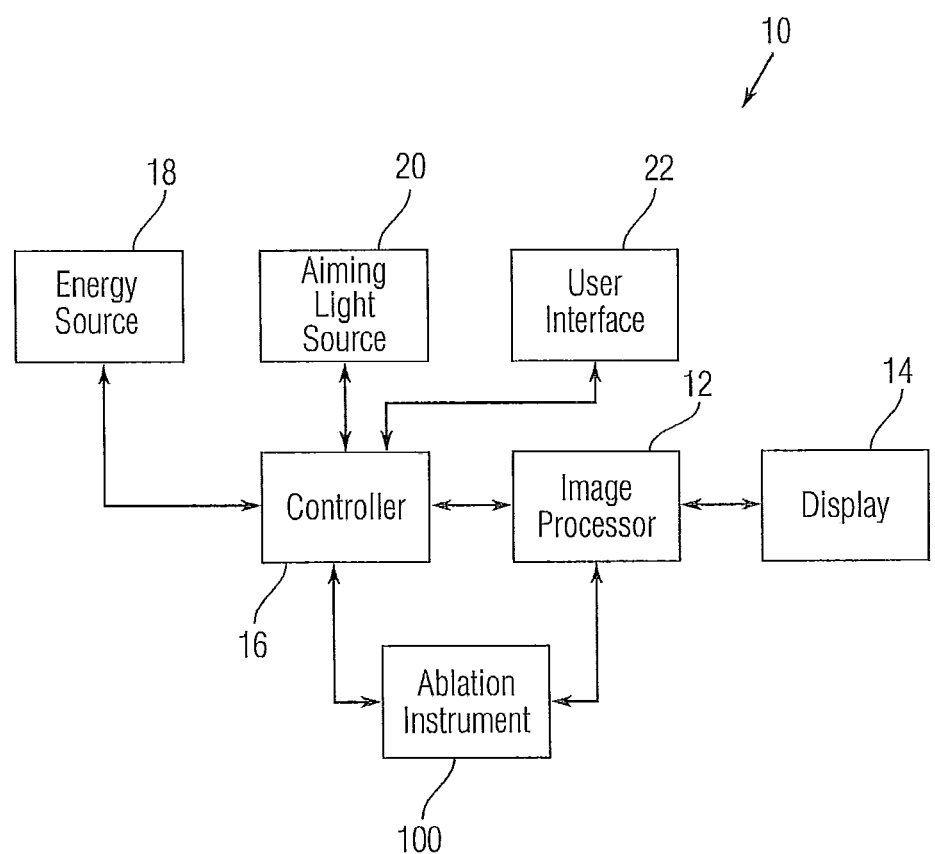
FIG. 1 is a block diagram depicting the components of an endoscope-guided cardiac ablation system according to the invention.

FIG. 1 is a schematic block diagram illustrating an ablator/endoscopic system in accordance with the invention, designated generally by reference numeral 10. Ablator system 10 preferably includes a surgical ablation instrument 100 preferably including an endoscope and ablation instrument as discussed below. The ablator system 10 further includes an aiming light source 20 and an illumination light source 24. A processor 12 designed to accept input and output data from the connected instruments, display and controller and process that data into visual information.

As will also be appreciated from the below discussion, an endoscope is preferably provided in ablation instrument 100 and has the capability of capturing both live images and recording still images. An illumination light is used to provide operating light to the surgical site. The illumination light is of a frequency that allows the user to differentiate between different tissues present at the operating site. An aiming light source 20 is used to visualize the location where energy will be delivered by the ablation instrument 100 to tissue. It is envisioned that the aiming light will be of a wavelength that can be recorded by an image capture device and visible on a display.

The processor 12 is designed to process live visual data as well as data from the ablation instrument controllers and display. The processor is configured execute a series of software and/or hardware modules configured to interpret, manipulate and record visual information received from the surgical site. The processor 12 is further configured to manipulate and provide illustrative and graphical overlays and composite or hybrid visual data to the display device. The image processor 12 has code executing on a processor that is operative to configure the image processor to generate an image of a lesion formed by ablation instrument 10 and determine the quality of the lesion based on operating information received from the ablation instrument 100.

Figure 2:
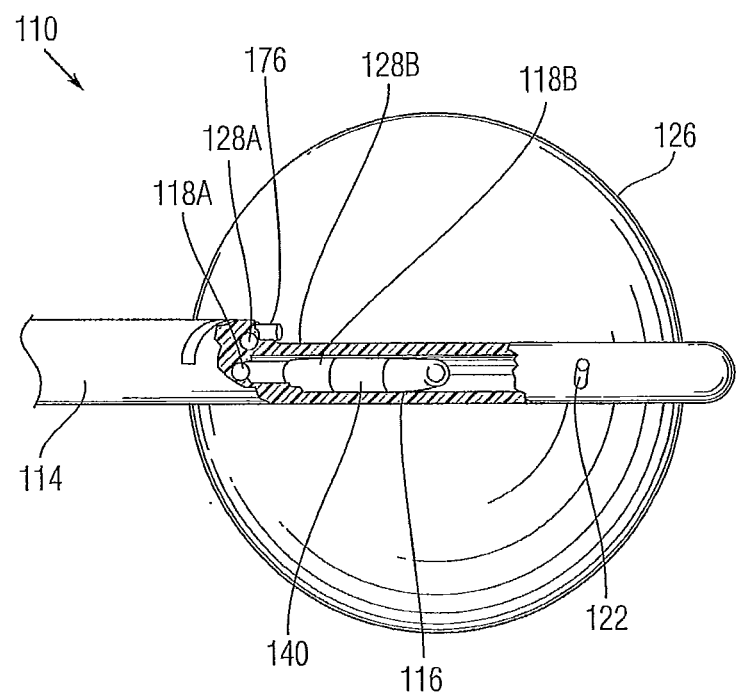
FIG. 2 is a schematic view of the of the cardiac ablation instrument of the cardiac ablation system of FIG. 1.

As seen in FIG. 2, the system 10 further includes a controller 16, an energy source 18, aiming light source 20 and a user interface 22. Controller 16 is preferably configured to determine the energy dispersion of an energy transmitter as well as determine the distance and movement of an energy transmitter relative to tissue at an ablation surgical site (as discussed further below). As will also be appreciated from the below discussion, an endoscope is preferably supported by the ablation instrument 100 and captures images that can be processed by the processor 12 to determine whether sufficient ablative have been directed to a specific area of a surgical site. Data obtained from the endoscope includes real-time video or still images of the surgical site as seen from the ablation instrument.

The aiming light source 20 is used to visualize the surgical site location 120 where energy will be delivered by the ablation instrument 100 to tissue 130. Preferably, the aiming light source 20 outputs light in a visible region of the electromagnetic spectrum. If a suitable ablation path is seen by the user, the controller 16 transmits radiant energy, via energy source 18, from the ablation instrument 100 to a target tissue site 120 to effect ablation by lesions. It is to be appreciated that the term "radiant energy" as used herein is intended to encompass energy sources that do not rely primarily on conductive or convective heat transfer. Such sources include, but are not limited to, acoustic, laser and electromagnetic radiation sources and, more specifically, include microwave, x-ray, gamma-ray, ultrasonic and radiant light sources. Additionally, the term "light" as used herein is intended to encompass electromagnetic radiation including, but not limited to, visible light, infrared and ultraviolet radiation.

The illumination light source is a light source used to provide proper illumination to the surgical site. The illuminate is configured so that natural biological tones and hues can be easily identifiable by an operator.

The controller 16 can provide the user with the ability to control the function of the aiming light source, the user input devices, and the ablation instrument. The controller serves as the primary control interface for the ablation system. Through the controller, the user can turn on and off both the aiming and illumination lights. Furthermore the controller possesses the ability to change the illumination and aiming light intensity. The ability to switch user interfaces or display devices is also envisioned. Additionally, the controller gives access to the ablation instrument, including control over the intensity of the discharge, duration and location of ablative energy discharges. The controller 16 can further provide a safety shutoff to the system in the event that a clear transmission pathway between the radiant energy source and the target tissue is lost during energy delivery (e.g., see commonly owned U.S.

patent application Ser. No. 12/896,010, filed Oct. 1, 2010, which is hereby incorporated by reference in its entirety.

The controller can be a separate microprocessor based control interface hardware or it can be a portion of a configured as a module operating through a processor based computer system configured to accept and control inputs from various physical devices.

Figure 3:
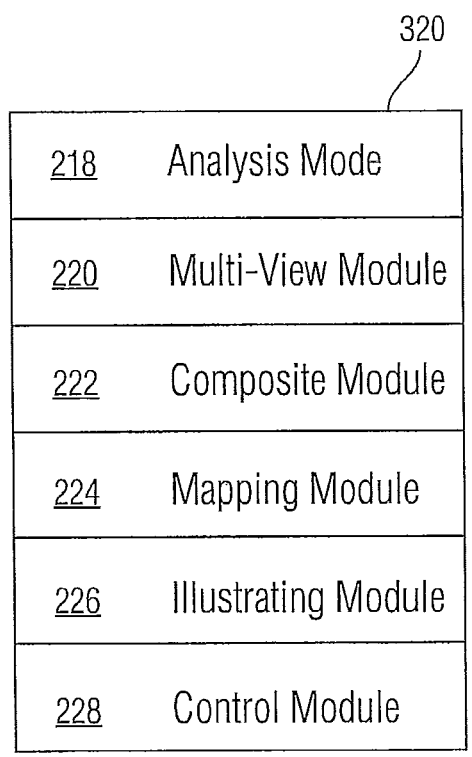
FIG. 3 is a block diagram of the processor modules used in the cardiac ablation instrument.

As shown in FIG. 3, a set of modules cooperate with one another to provide the information presented through the interface of FIG. 2. Thus, for example, there is an analysis module 218, a multiple view module 220, a composite module 222, a mapping module 224, an illustrating module 226, and a control interface module 228. Each of these modules can comprise hardware, code executing in a processor, or both, that configures a machines such as a workstation to implement the functionality described herein.

With further reference to FIG. 3, the analysis module 218 includes instructions for analyzing a lesion and determining if it is sufficient for the desired treatment. The analysis module is configured to inspect the image data captured by the image capture device and a lesion of sufficient dimensions and quality has been formed. The analysis module 218 can be implemented as discrete sub-modules to provide functions such as receiving data on the duration and intensity of an ablative emission. An additional sub module is capable of evaluating the duration of the energy emission and comparing it to a look up table of sufficient duration and intensity values suitable to form a proper lesion.

The multiple view module 220 includes instructions for configuring the processor 12 to provide multiple images to the display. The multiple view module configures the display to depict at least two image depiction areas. In a first image depiction area, the live video stream of the surgical site is displayed to the user. In a second image depiction area, a still image, highlighting the last target of ablative energy is depicted.

The composite module 222 includes instructions for combining a series of still images and producing a composite image that depicts the target location of the ablative emission in each still image. The compositing module 222 can be implemented as discrete sub-modules to provide functions such as altering the transparency of each still image layer of the composite image so that a time based map of ablation locations can be produced. Another function implemented by the submodules is construction of a video or slideshow from a sequence of still images.

The mapping module 224 includes instructions for overlaying proposed treatment paths on the live image. The mapping module is configured to show colored markers indicating acceptable levels of ablative energy depositing. For example the mapping module is capable of generating a green colored visual marker and superposing it over the live image to indicate areas that have yet to receive levels of ablative energy necessary for treatment. Conversely, the mapping module 224 is also capable of simultaneously generating a red colored (or other color) visual marker and superimposing it over the live image to indicate areas that have received sufficient quantities of ablative energy suitable lesions. The mapping module 224 can be implemented as discrete sub-modules to provide functions such as receiving data on the duration and intensity of an ablative emission and correlating that specific instance to a specific stored image.

Figure 8:
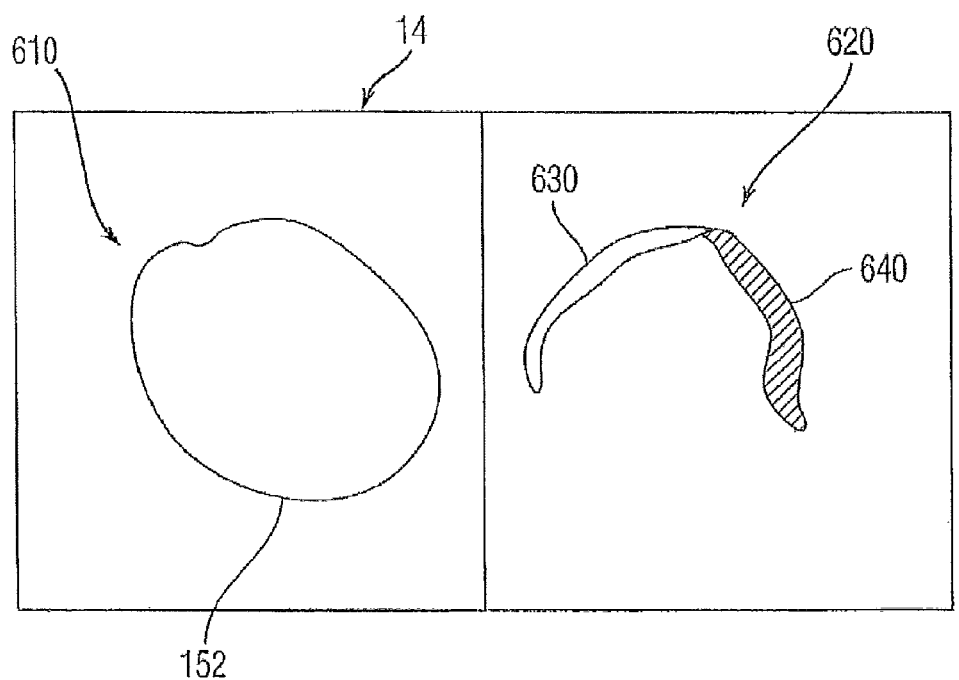
FIG. 8 is a screen shot of the display of FIG. 1 depicting visual warning signals indicative of insufficient lesions.

The illustrating module 226 includes instructions for providing a image to the display, wherein the image is an illustration or graphical representation of the surgical site. The illustrating module 226 is configured to allow annotation of the illustrated image as well as comparison between the live image and the illustrated image. For example, and as shown in FIG. 8, display 14 provides a first screen portion 610 depicting the actual surgical site 152 as viewed from endoscope 176. Display 14 also illustrates a second screen portion 620 illustrating a graphical depiction of the surgical site 152 indicating the actual path of the energy transmitter 140 on the tissue at the surgical site wherein the path consists of a trace indicating the sufficiency of the formed lesions in which a solid trace 630 indicates sufficient lesions and a hashed trace 640 indicates insufficient lesions.

The control module 220 includes instructions for orientating and accessing the functions of each of the other modules, as well as communicating with the controller and inputting information or manipulating the parameters of the data being displayed during operation. The manipulation and controlling functions can be implemented as discrete sub-modules with instructions for selecting operation modes, control interfaces, display orientation, recording modes, storage device location and data entry.

Figure 4:
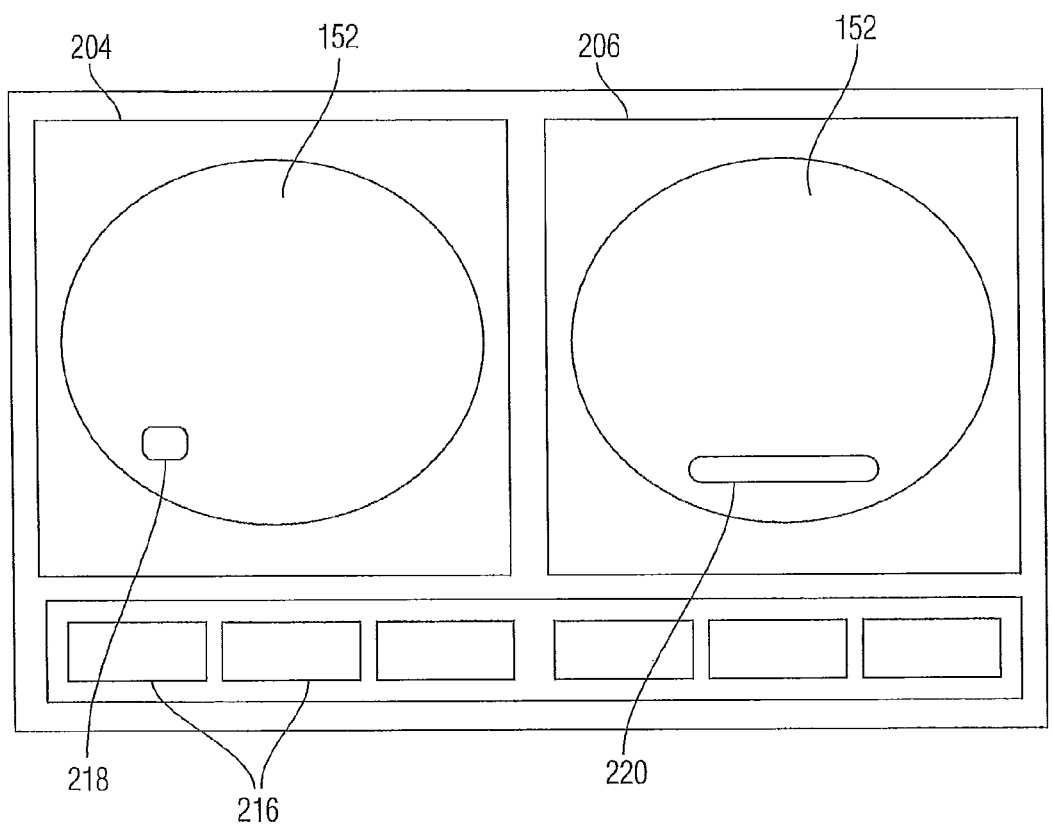
FIG. 4 illustrates a user interface in the form of a splint-screen arrangement for displaying information.

The user refers to the live video feed from the image capture device to determine where to direct a radiant energy transmission. Upon first use of the device, a live video image and a still image of the surgical site are depicted on the display. As seen in FIG. 4, the processor 12 outputs to the display 14 at least two separately defined image depiction areas 204, 206. One image depiction area 204 is reserved for displaying live video transmitted from the surgical site 152. At least one other image depiction area 206 is used to depict an image or a composite image comprised of several still images representing specific moments in time during the surgical procedure.

The live video shown to the user will allow the user to see the reflection of the aiming light 218 and hence direct ablative energy. It is envisioned that the first still image 210 depicted will be a still image captured at a point in time prior to the initiation of the first radiant energy emission. For instance, at a point in time prior to the emission of radiant energy, the image capture device records an image 210 of the surgical site 152 that depicts the surgical site 152 without the aiming light. By taking a still image 210 of the site, the user can record a baseline image of the surgical site before any treatment has been commenced. Furthermore, through the functions of the illustrative module, an illustration of the untouched 152 can be generated. During emission of radiant energy a still image 210 is taken of the surgical site 152. The characteristics of the ablative event (e.g. information regarding the duration and intensity of the radiant of the energy emission) are stored and associated with the image depicting that specific emission. In addition, the reflection of the aiming light will be visible in the still image, providing a location indicator as to where the energy was directed. A series of these still images can be combined by using the composite module. By modifying the opacity of each image, the reflected light of the aiming light for each ablative event will be visible in the composite image. In this way, a complete record 220 of where energy was directed will becomes available. Furthermore, because the composite image is composed a series of individual images representing a specific period of time during the procedure, a time based map of the entire operation can also be produced in real time or for subsequent review.

Also visible in FIG. 4 are control interfaces 216 for accessing the control module. The control interfaces allow the user to select image style and opacity as well and initiating the functions of the other modules. Furthermore the functions of the controller 16 are also controllable from the control interface.

It is to be appreciated the invention is not to be understood to be limited to the two image depiction areas discussed above with reference to FIG. 3 or 4, but rather may encompass any number of image depiction areas in which the images and representations of the surgical site 152 can be reviewed. With reference to FIG. 8 the images shown by the display 14 can be manipulated by the modules to illustrate the presence of sufficient or insufficient lesion formation. For instance, the display 14 may illustrate the image of the surgical site 152 viewed from the endoscope 176 wherein varying shades of grey and white depict tissue and lesions and in the event insufficient lesions are determined to be formed, or a red marker can be superimposed on the image of the surgical site 152 at the location where the insufficient lesion was determined. Coincidently, an audio signal may also be emitted from ablator system 10 causing further warning to the user.

Therefore, if the user is not satisfied with the quality of the lesion produced, or the modules indicate that a sufficient lesion was not produced, the user can promptly redo the treatment of a specific tissue location (spot treatment). Conversely, if the modules indicate that a sufficient lesion was formed, the user can confidently move on to a new tissue location to continue the treatment thus saving time and effort by avoiding the need to more closely examine the tissue location that was just treated. Hence, once the entire treatment is performed, the modules of the system permit the surgeon to view all treatment segments forming the entire ablation arc to see if a continuous, uninterrupted ablation has been formed (or see if the ablation has the intended, desired shape). If there are visible gaps or other imperfections with the formed ablation, the surgeon can move the energy transmitter 140 to the proper location for retreatment of these areas until the desired ablation is formed. The process can then be repeated to determine and confirm that the gap was eliminated.

As a result, the mapping, analyzing and illustrating functions performed by the ablation system of the present invention overcome the disadvantages associated with prior ablation surgical procedures and results in increased ablation success rates due to a more optimal and more accurate viewing and quality determination of the spot lesions created to form the continuous ablation at the tissue location for the surgical site 152.

With reference now to FIG. 5, a description of ablation instrument 100 is provided. FIG. 5 provides a schematic, cross-sectional view of an ablation instrument 100, including an elongate body 114, a central lumen tubing 116 and a compliant balloon 126 inflatable via one or more ports 122 in the central tubing 116. The central tubing 116 can also house an energy emitter that is capable of both axial movement and rotation within a lumen formed in the elongate body 114. Additionally formed in the elongated body 114 (also referred to herein as the catheter body) there can be a plurality of additional lumens, through which certain devices or instruments can be passed. For example, the catheter body 114 also provides lumens 118A and 118B for extraction (or circulation) of an inflation fluid, an endoscope 176 and illuminations fibers 128A and 128B.

It should be understood that the embodiments illustrated in the drawings are only a few of the cardiac ablation instruments that can be utilized in accordance with the present invention. Further descriptions of other embodiments can be found, for example, in commonly owned, co-pending U.S. patent application Ser. No. 10/357,156, filed Feb. 3, 2003, U.S. patent application Ser. No. 09/924,393, filed Aug. 7, 2001 and which is expressly incorporated by reference.

With reference now to FIGS. 5-6, the ablation instrument 100 is preferably designed such that upon disposition within the heart (e.g., proximal to a pulmonary vein), the balloon 126 can be inflated such that a shoulder portion 150 of the balloon 126 will be urged into close proximity with a target region 152 of cardiac tissue. As shown in FIG. 4, the energy emitter (or "lesion generator") 140 can be positioned to delivery ablative energy to the target region 152 to form a continuous lesion. The term "continuous" in the context of a lesion is intended to mean a lesion that substantially blocks electrical conduction between tissue segments on opposite sides of the lesion.

The radiant energy emitter 40 is shown in FIG. 5 disposed within the balloon 26 remotely from the target tissue (e.g., within a central lumen 116 of the catheter body 114 or otherwise disposed within the balloon). In one illustrated embodiment, the radiant energy transmitter (ablation element) 140 includes at least one optical fiber coupled to a distal light projecting, optical element, which cooperate to project a spot of ablative light energy through the instrument 100 to the target site 152. The catheter body 114, projection balloon 126 and inflation/ablation fluids are all preferably substantially transparent to the radiant energy at the selected wavelength to provide a low-loss transmission pathway from the radiant energy transmitter 140 to the target site 152. It should be understood that the term "balloon" encompasses deformable hollow shapes which can be inflated into various configurations including spherical, obloid, tear drop, etc., shapes dependent upon the requirements of the body cavity. Such balloon elements can be elastic or simply capable of unfolding or unwrapping into an expanded state. The balloon can further encompass multiple chamber configurations.

Also disposed within the instrument 100 is a reflectance sensor, preferably an endoscope 176 capable of capturing an image of the target site 152 and/or the instrument position. The endoscope 176 is typically an optical fiber bundle with a lens or other optical coupler at its distal end to receive light. The reflectance sensor/endoscope can also include an illumination source, such one or more optical fibers coupled to a light source or sources. Endoscopes are available commercially from various sources. The endoscope can further include an optical head assembly, as detailed in more detail below, to increase the field of view. In one illustrated embodiment, ablation element 140 and endoscope 176 are adapted for independent axial movement within the catheter body 14.

The term "endoscope" as used herein is intended to encompass optical imaging devices, generally, including but not limited to endoscopes, fiberscopes, cardioscopes, angioscopes and other optical fiber-based imaging devices. More generally, "endoscope" encompasses any light-guiding (or waveguide) structure capable of transmitting an "image" of an object to a location for viewing, such as display 14.

Preferably, spot lesions are formed at the target site 152 by applying radiant energy from the energy transmitter 140 to target tissue. The applied radiant energy may be applied in an energy range from about 50 Joules/$cm^2$ to about 1000 Joules/$cm^2$, or preferably from about 75 Joules/$cm^2$ to about 750 Joules/$cm^2$. The power levels applied by the energy emitter can range from about 10 Watts/$cm^2$ to about 150 Watts/$cm^2$ and the duration of energy delivery can range from about 1 second to about 1 minute, preferably from about 5 seconds to about 45 seconds, or more preferably from about 10 to about 30 seconds. For example, for power levels between 10 and 75 Watts/$cm^2$ it can be advantageous to apply the radiant energy for about 30 seconds. Lesser durations, e.g., of 10 to 20 seconds, can be used for power levels of 75 to 150 Watts/$cm^2$. It is to be understood the above figures are provided as examples and the energy, power and time duration figures set forth above are provided merely as examples and are not to be understood to be limited thereto.

In the illustrated embodiment of the ablation instrument 100 shown in FIGS. 5-6, the energy emitter 140 is a radiant energy emitter including at least one optical fiber coupled to a distal light projecting optical element, which cooperate to project a spot of ablative light energy through the instrument 100 to the target site 152. The optical element can further comprise one or more lens elements and/or refractive elements capable of projecting a spot or arc-shaped beam of radiation. Alternatively, the lesion generator may generate an annulus or partial ring of ablative radiation, as described in more detail in commonly owned U.S. Pat. No. 6,423,055 issued Jul. 22, 2002, herein incorporated by reference for its disclosure related thereto.

Since the radiant energy (e.g., a laser) emitted from the energy emitter 140 is typically outside the visual light spectrum that can be detected by the human eye, the ablation instrument 100 includes an aiming light preferably having a pulsed operating mode in which visible light from the aiming light unit is delivered in pulses to cause intermittent illumination of the tissue at the target site 152. This gives the aiming light an appearance of being a blinking light. By delivering the visible aiming light in pulses, the surgeon is able to directly observe the tissue that is being treated at the target site 152, using an endoscope, between the aiming light pulses.

During a surgical ablation procedure, the endoscope 176 is used to determine the extent of tissue ablation by sensing the change in color of the tissue as it is ablated and at a time when the aiming beam is in an off cycle via the display 14. In other words, between the blinking (pulses) of the aiming light, the surgeon can observe the treated tissue to determine how the treatment is progressing since the endoscope 176 is used to determine the extent of tissue ablation by sensing the change in color of the tissue as it is ablated and at a time when the aiming beam is in an off cycle. However, many conditions may cause the actual detection of change in color of tissue being ablated to be difficult and/or unreliable in regards to whether proper spot lesions are formed by the energy transmitter 140 on the tissue at the ablation surgical site 152. For instance, insufficient illumination at the surgical site 152 can make it difficult, if not impossible, to ascertain whether proper spot lesions were formed at the surgical site as viewed on display 14.

Figure 7:
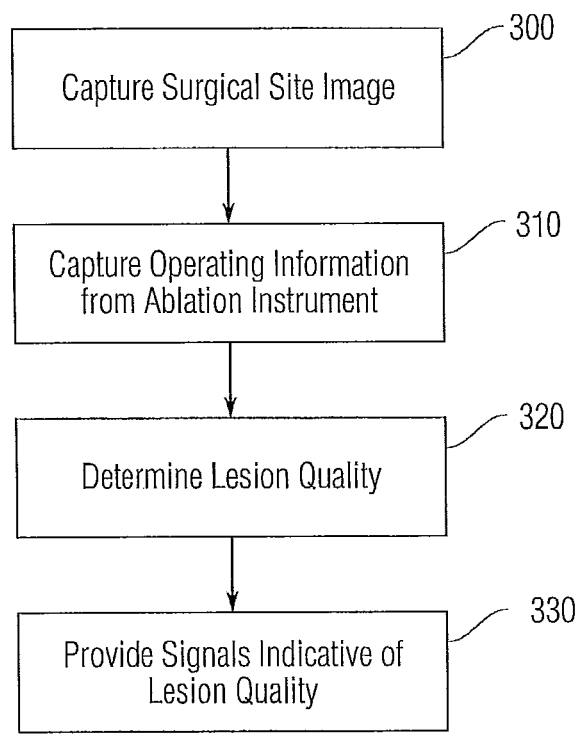
FIG. 7 is a flow diagram illustrating the steps performed by the ablator system of FIG. 1 for determining the quality of lesions formed during a surgical ablation procedure.

The processor 12 of ablator system 10 obviates this problem by determining the quality of the lesion formed on the tissue at the target site 152 which may be viewed on monitor 14 and/or indicated to a surgeon visual overlay or audio cues. With reference now to the flow diagram of FIG. 7, the method of operation for determining the quality of spot lesions at an ablation surgical site 152 will now be discussed.

Starting at step 300, the processor 12 captures the image from endoscope 176 of the tissue being ablated at the surgical site. At step 310, the processor 12 also captures information relating to the energy transmitter 140 from controller 16. The captured operating information for the energy transmitter 140 can include, as non-limiting examples: the amount of radiant energy (power) emitted by energy transmitter 140; any reflectance data of energy returning from the tissue at the surgical site 152; the distance the energy transmitter 140 is from tissue to be ablated; the time of application of energy to any one target site; the rate of movement of the energy transmitter 140 from one location to another as ablation continues at the surgical site 152; and the distance between one location at which energy is delivered to the next location of energy delivery. The captured energy transmitter 140 information includes: the amount of radiant energy (power) applied by energy transmitter 140 on the tissue at the surgical site 152 to form spot lesions; the distance the energy transmitter 140 is from tissue to be ablated via spot lesions; and the rate of movement of energy transmitter 140 relative to the tissue at the surgical site 152. It is to be appreciated that aforesaid information captured regarding energy transmitter 140 is not to be understood to be limited thereto as more or less information may be captured that is necessary to determine the quality of the spot lesions formed on the tissue at the surgical site.

The processor 12 then preferably uses algorithmic techniques to determine whether a sufficient spot lesion has just recently been formed on the tissue at the surgical site (step 320). In other words, given the captured operating information such as the distance the energy transmitter 140 is located from the tissue at the surgical site 152, the rate of movement of the energy transmitter 140 relative to the tissue at the surgical site 152 (e.g., the amount of time that energy is applied to the tissue at a given location), and the amount of energy being applied, a determination is made by the image processor 12 as to whether a sufficient spot lesion has been formed on the tissue at a location which the energy transmitter 140 has just applied ablation enemy thereto. As one example, the algorithm can take into account the fact that amount of energy emitted will differ from the amount of energy delivered to tissue due to intervening factors (e.g., travel through an liquid), the distances along which the energy travels from the emitter, estimates of resistances presented by any intervening fluids, and any feedback concerning changes in the albedo of the tissue, as may be determined based on pre-operative captured data or information in a lookup table, can be used by image processor 12, in any combination, as coefficients to gauge the amount of power actually delivered to a particular target location as opposed to the amount of power that was intended to be delivered (which is always greater). In other words, given the distance the energy transmitter 140 is located from the tissue at the surgical site 152, the rate of movement of the energy transmitter 140 relative to the tissue at the surgical site 152 (e.g., the amount of time that energy is applied to the tissue at a given location), and the amount of energy being applied, a determination is made as to whether a sufficient spot lesion has been formed on the tissue at a location which the energy transmitter is applying ablation energy thereto. A lookup table or other similar means may also be used by processor 12 for determining the aforesaid lesion quality. A spot lesion is to be understood as being sufficient when it comprises enough scar tissue effective to block the transmission of electrical signals therethrough.

The processor 12 is preferably further operative and configured to provide a signal to the surgeon indicative of whether a sufficient spot lesion has been formed (step 330). This indicative signal may be provided in the event an insufficient or no spot lesion was formed on the tissue at the surgical site 152 that was subject to the energy transmitter 140 dispersing energy thereto. This indicative signal may be an audio and/or visual signal. The audio signal may consist of a warning tone and the visual signal may consist of a marker (e.g., color red) superimposed on the display 14 illustrating the surgical site 152 (provided via endoscope 176) at the location at which the insufficient spot lesion was determined. Thus, when image processor 12 determines an insufficient spot lesion has been formed, the aforesaid warning signal is promptly provided to the surgeon enabling the surgeon to revisit the tissue having the insufficient lesion and make proper adjustments with the energy transmitter 140 (e.g., apply more energy, close the distance between energy transmitter 140 and the surgical site and/or slow the movement of energy transmitter 140 relative to the surgical site) so as to now form sufficient lesions.

Figure 9:
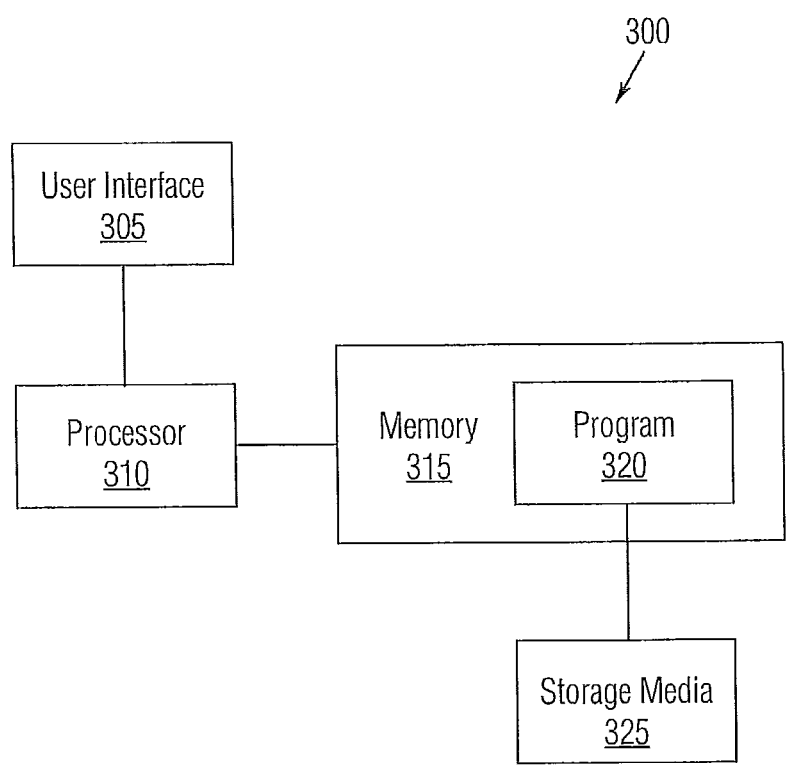
FIG. 9 is a block diagram of a computer system configured to employ the ablation method of the present invention.

FIG. 9 is a block diagram of a computer system 300 configured for employment of method 100. System 300 includes a user interface 305, a processor 310, and a memory 315. System 300 may be implemented on a general purpose microcomputer, such as one of the members of the Sun® Microsystems family of computer systems, one of the members of the IBM® Personal Computer family, one of the members of the Apple® Computer family, or a myriad other conventional workstations. Although system 300 is represented herein as a standalone system, it is not limited to such, but instead can be coupled to other computer systems via a network (not shown).

Memory 315 is a memory for storing data and instructions suitable for controlling the operation of processor 310. An implementation of memory 315 would include a random access memory (RAM), a hard drive and a read only memory (ROM). One of the components stored in memory 315 is a program 320.

Program 320 includes instructions for controlling processor 310 to execute method 100. Program 320 may be implemented as a single module or as a plurality of modules that operate in cooperation with one another. Program 320 is contemplated as representing a software embodiment of the method described hereinabove.

User interface 305 includes an input device, such as a keyboard, touch screen, tablet, or speech recognition subsystem, for enabling a user to communicate information and command selections to processor 310. User interface 305 also includes an output device such as a display or a printer. In the case of a touch screen, the input and output functions are provided by the same structure. A cursor control such as a mouse, track-ball, or joy stick, allows the user to manipulate a cursor on the display for communicating additional information and command selections to processor 310.

While program 320 is indicated as already loaded into memory 315, it may be configured on a storage media 325 for subsequent loading into memory 315. Storage media 325 can be any conventional storage media such as a magnetic tape, an optical storage media, a compact disc, or a floppy disc. Alternatively, storage media 325 can be a random access memory, or other type of electronic storage, located on a remote storage system.

The methods described herein have been indicated in connection with flow diagrams that facilitate a description of the principal processes; however, certain blocks can be invoked in an arbitrary order, such as when the events drive the program flow such as in an object-oriented program. Accordingly, the flow diagram is to be understood as an example flow and that the blocks can be invoked in a different order than as illustrated.

It should be understood that various combination, alternatives and modifications of the present invention could be devised by those skilled in the art. The present invention is intended to embrace all such alternatives, modifications and variances that fall within the scope of the appended claims.

Although described in connection with cardiac ablation procedures, it should be clear that the instruments and systems of the present invention can be used for a variety of other procedures where treatment with radiant energy is desirable, including laparoscopic, endoluminal, perivisceral, endoscopic, thoracoscopic, intra-articular and hybrid approaches.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed:

1. A tissue ablation system for identification of lesions formed by directed energy emission at a surgical site, the tissue ablation system comprising:
   a tissue ablation instrument for use at the surgical site and having:
      a directed energy emitter movably disposed within a lumen of a catheter and configured to emit a variable amount of directed radiant ablative energy for delivering an amount of the radiant ablative energy to tissue at the surgical site to form a lesion; an aiming light, an illumination light;
   an endoscope configured to capture live video and still images;
      a controller configured to control the variable amount of directed radiant ablative energy and to direct the energy emitter within the surgical site and to determine operating information, wherein the operating information includes: an amount of radiant energy emitted by the directed energy emitter, a distance the directed energy emitter is from the tissue at the surgical site, and a rate of movement of the directed energy emitter relative to the tissue at the surgical site; and
   a computer having a processor, database and a display; and a plurality of modules executing in the processor so as to configure the computer to perform operations including accessing data from an access module, the plurality of modules further including: an analysis module configured to perform analysis of the live video and still images from the endoscope and the operating information from the controller and based on the analysis to determine whether the dimensions of the lesion and the amount of radiant ablative energy delivered by the directed energy emitter to the lesion are effective to form enough scar tissue in the lesion to block electrical conduction between tissue segments on opposite sides of the lesion at the surgical site, wherein the analysis further includes reflectance data of changes in lesion albedo;
   a composite module for creating a composite image comprised of a series of still images taken during each emission of the directed radiant ablative energy; and a split-screen module for simultaneously displaying the live video image and the composite image or one of the still images;
   the processor further configured to provide a signal to a user of the tissue ablation instrument indicating whether a lesion formed by the tissue ablation instrument at the surgical site is determined by the analysis module to be effective to block the conduction of electrical signals at the surgical site.

2. A tissue ablation system as in claim 1, further comprising, among the plurality of modules, a mapping module for providing a visual marker on the still image corresponding to the location of at least one lesion.

3. A tissue ablation system as in claim 1, further comprising, among the plurality of modules, an illustration module operative to provide the display with illustrations of the surgical site and to indicate whether the lesions formed by said tissue ablation instrument at said surgical site are determined by the analysis module to be effective to block the conduction of electrical signals at the surgical site.

4. A tissue ablation system as in claim 1, wherein the aiming light is further configured to reflect different frequencies of light depending on a tissue type illuminated.

5. A tissue ablation system as in claim 1, wherein opacity of each of the series of the still images in the composite image can be individually set.

6. A tissue ablation system as in claim 1, wherein the aiming light is visible in each still image of the composite image.

7. A tissue ablation system as recited in claim 1, wherein said signal is an audio signal provided when the formed lesion at said surgical site is determined by the analysis module to not be effective to block the conduction of electrical signals at the surgical site.

8. A tissue ablation system as recited in claim 1, wherein said signal is a visual signal provided on a display accessible by a user of said tissue ablation instrument.

9. A tissue ablation system as recited in claim 8, wherein said visual signal is a marker trace indicating a lesion that is determined by the analysis module to not be effective to block conduction of electrical signals at the surgical site.

10. A tissue ablation system as recited in claim 8, wherein said marker trace consists of a colored trace.

11. A tissue ablation system as recited in claim 8, wherein said marker trace is superimposed on the composite or still image depicting the surgical site.

\* \* \* \* \*